(12) United States Patent
Cumming

(10) Patent No.: US 8,734,512 B2
(45) Date of Patent: May 27, 2014

(54) BIASED ACCOMMODATING INTRAOCULAR LENS

(76) Inventor: James Stuart Cumming, Laguna Beach, CA (US)

(*) Notice: Subject to any disclaimer, the term of this patent is extended or adjusted under 35 U.S.C. 154(b) by 0 days.

(21) Appl. No.: 13/472,893

(22) Filed: May 16, 2012

(65) Prior Publication Data

US 2012/0310344 A1 Dec. 6, 2012

Related U.S. Application Data

(60) Provisional application No. 61/519,098, filed on May 17, 2011.

(51) Int. Cl.
*A61F 2/16* (2006.01)

(52) U.S. Cl.
USPC ........ 623/6.44; 623/6.37; 623/6.46; 623/6.47

(58) Field of Classification Search
USPC ........... 623/6.37, 6.38, 6.44, 6.45, 6.46, 6.47, 623/6.49, 6.51, 6.11, 6.18, 6.39, 6.43
See application file for complete search history.

(56) References Cited

U.S. PATENT DOCUMENTS

| | | |
|---|---|---|
| 2,834,023 A | 5/1958 | Wolfgang |
| 4,073,014 A | 2/1978 | Poler |
| 4,118,808 A | 10/1978 | Poler |
| 4,122,556 A | 10/1978 | Poler |
| 4,159,546 A | 7/1979 | Shearing |
| 4,168,547 A | 9/1979 | Konstantinov et al. |
| 4,173,798 A | 11/1979 | Welsh |
| 4,174,543 A | 11/1979 | Kelman |
| 4,206,518 A | 6/1980 | Jardon et al. |
| 4,244,060 A | 1/1981 | Hoffer |
| 4,254,509 A | 3/1981 | Tennant |
| 4,277,851 A | 7/1981 | Choyce et al. |
| 4,298,995 A | 11/1981 | Poler |
| 4,304,012 A | 12/1981 | Richard |
| 4,409,690 A | 10/1983 | Gess |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,629,462 A | 12/1986 | Feaster |
| 4,664,665 A | 5/1987 | Reuss et al. |
| 4,664,666 A | 5/1987 | Barrett |
| 4,673,406 A | 6/1987 | Schlegel |
| 4,681,102 A | 7/1987 | Bartell |
| 4,704,123 A | 11/1987 | Smith |
| 4,710,195 A | 12/1987 | Glovinazzo |
| 4,718,904 A | 1/1988 | Thornton |

(Continued)

FOREIGN PATENT DOCUMENTS

| | | |
|---|---|---|
| DE | 3626869 | 2/1988 |
| FR | 2728458 | 6/1996 |

(Continued)

*Primary Examiner* — David H Willse
*Assistant Examiner* — Javier Blanco
(74) *Attorney, Agent, or Firm* — Knobbe Martens Olson & Bear LLP

(57) ABSTRACT

An accommodating intraocular lens has a lens optic that is coupled to at least one haptic and is anteriorly biased with respect thereto.

4 Claims, 3 Drawing Sheets

(56) References Cited

U.S. PATENT DOCUMENTS

| | | |
|---|---|---|
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,769,033 A | 9/1988 | Nordan |
| 4,769,035 A | 9/1988 | Kelman |
| 4,778,463 A | 10/1988 | Hetland |
| 4,781,719 A | 11/1988 | Kelman |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,601 A | 6/1989 | Smith |
| 4,846,833 A | 7/1989 | Cumming |
| 4,862,885 A | 9/1989 | Cumming |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,141,507 A | 8/1992 | Paraekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,674,282 A | 10/1997 | Cumming |
| 5,699,142 A | 12/1997 | Lee et al. |
| 5,800,532 A | 9/1998 | Lieberman |
| 5,837,156 A | 11/1998 | Cumming |
| 5,843,187 A | 12/1998 | Bayers |
| 5,873,879 A | 2/1999 | Figueroa et al. |
| 5,919,230 A | 7/1999 | Sambursky |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 | 3/2001 | Cumming |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |
| 6,503,275 B1 | 1/2003 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,540,353 B1 | 4/2003 | Dunn |
| 6,558,420 B2 | 5/2003 | Green |
| 6,613,343 B2 | 9/2003 | Dillingham et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Willse |
| 6,695,881 B2 | 2/2004 | Peng et al. |
| 6,749,634 B2 | 6/2004 | Hanna |
| 6,767,363 B1 | 7/2004 | Bandhauer et al. |
| 6,849,091 B1 | 2/2005 | Cumming |
| 6,858,040 B2 | 2/2005 | Nguyen et al. |
| 6,881,225 B2 | 4/2005 | Okada |
| 6,884,263 B2 | 4/2005 | Valyunin |
| 6,921,416 B2 | 7/2005 | Khoury |
| 6,926,736 B2 | 8/2005 | Peng |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |

(56) References Cited

U.S. PATENT DOCUMENTS

| | | |
|---|---|---|
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,523,942 B2 | 9/2013 | Cumming |
| 2001/0001836 A1 | 5/2001 | Cumming |
| 2002/0120329 A1 | 8/2002 | Lang et al. |
| 2003/0060881 A1 | 3/2003 | Glick et al. |
| 2003/0078658 A1 | 4/2003 | Zadno-Azizi |
| 2003/0097177 A1 | 5/2003 | Tran |
| 2003/0109925 A1 | 6/2003 | Ghazizadeh et al. |
| 2003/0135272 A1 | 7/2003 | Brady et al. |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0111152 A1 | 6/2004 | Kelman |
| 2004/0148023 A1 | 7/2004 | Shu |
| 2004/0249456 A1 | 12/2004 | Cumming |
| 2005/0021140 A1 | 1/2005 | Liao |
| 2005/0027354 A1 | 2/2005 | Brady et al. |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064162 A1 | 3/2006 | Klima |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0032867 A1 | 2/2007 | Cumming |
| 2007/0129800 A1 | 6/2007 | Cumming |
| 2007/0129803 A1* | 6/2007 | Cumming et al. ............ 623/6.28 |
| 2007/0135915 A1* | 6/2007 | Klima .......................... 623/6.37 |
| 2007/0198084 A1 | 8/2007 | Cumming et al. |
| 2008/0027538 A1 | 1/2008 | Cumming |
| 2008/0027539 A1 | 1/2008 | Cumming |
| 2008/0027540 A1 | 1/2008 | Cumming |
| 2008/0046077 A1 | 2/2008 | Cumming |
| 2008/0086208 A1 | 4/2008 | Nordan |
| 2008/0154362 A1 | 6/2008 | Cumming |
| 2008/0281415 A1 | 11/2008 | Cumming |
| 2008/0281416 A1 | 11/2008 | Cumming |
| 2008/0288066 A1 | 11/2008 | Cumming |
| 2008/0294254 A1 | 11/2008 | Cumming et al. |
| 2008/0319545 A1 | 12/2008 | Cumming |
| 2009/0005866 A1 | 1/2009 | Cumming |
| 2010/0004742 A1 | 1/2010 | Cumming |
| 2011/0313519 A1 | 12/2011 | Cumming |
| 2011/0313524 A1 | 12/2011 | Cumming |
| 2011/0313525 A1 | 12/2011 | Cumming |
| 2011/0313526 A1 | 12/2011 | Cumming |
| 2013/0073039 A1 | 3/2013 | Mirlay |

FOREIGN PATENT DOCUMENTS

| | | |
|---|---|---|
| FR | 2728459 | 6/1996 |
| FR | 2734472 | 11/1996 |
| FR | 2765797 | 1/1999 |
| GB | 2171912 | 9/1986 |
| GB | 2226246 | 6/1990 |
| JP | 681687 | 5/1993 |
| JP | 2003-190193 | 7/2003 |
| WO | WO 93/05733 | 4/1993 |
| WO | WO 01/19288 | 3/2001 |
| WO | WO 01/19289 | 3/2001 |
| WO | WO 2007/037180 | 4/2007 |

* cited by examiner

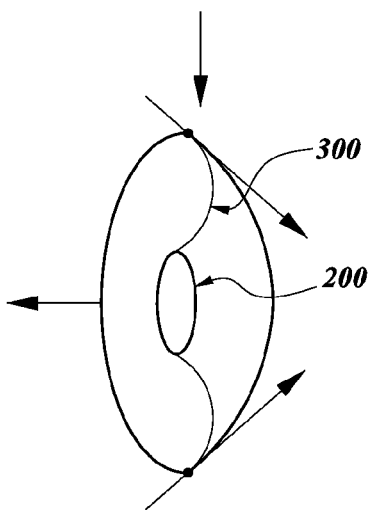
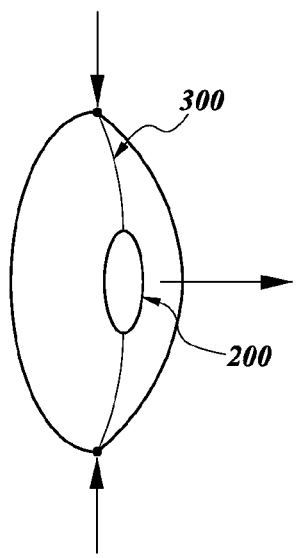
Anterior Vault            Posterior Vault
FIG.3A                    FIG.3B

BIASED ACCOMMODATING INTRAOCULAR LENS

CROSS-REFERENCE TO RELATED APPLICATIONS

This application is based on U.S. Provisional Application No. 61/519,098, filed on May 17, 2011, the contents and disclosures of which are fully incorporated herein by reference.

BACKGROUND OF THE INVENTION

Premium intraocular lenses (IOLs) implanted during cataract surgery are categorized three ways: accommodating, multifocal and toric intraocular lenses.

The best visual acuity is achieved with the single focus accommodating lenses. The optic of these lenses moves forward and backward upon constriction and relaxation of the ciliary muscle. However, for reading in dim lighting conditions, or for small print, week reading glasses are often necessary.

The multifocal lenses focus light on the retina at either two or three focal lengths. Thus, there is more than one image on the retina simultaneously. This creates problems since the amount of light in focus is divided between the multiple focal points, and contrast sensitivity is thereby reduced, making vision at all distances difficult in dim lighting. In addition, there are severe problems when driving at night when the pupil is dilated. Many patients experience severe glare and halos and many have had to have the multifocal lenses explanted and replaced with a single vision standard lens, because of this problem. However, the near vision with the multifocal lenses is superior to that of the current accommodating lens.

The toric lenses correct the eyes that have significant astigmatism.

The currently marketed plate accommodating intraocular lenses provide excellent distance and intermediate vision but sometimes require weak, +1.00, reading glasses for prolonged reading, for seeing small print, or reading in dim lighting conditions.

Furthermore, it is important for intraocular lenses to have a consistent location along the axis of the eye to provide good uncorrected distance vision and to center in the middle of the vertical meridian of the eye. Without excellent uncorrected distance vision there is no point in implanting lenses designed to give seamless vision from far to near.

The original intraocular lens consisted of a single optic. These lenses frequently de-centered and dislocated and it was discovered that there was a need to center and fixate the lens optic in the vertical meridian of the eye.

Attachments to the optic that center and fixate the lens within the capsular bag are called haptics. Traditionally, haptics consist of multiple flexible loops of various designs, J loops, C loops, closed loops and flexible radial arms. Recently, traditional haptics have been replaced in some lens designs with oblong, flat flexible plates, called plate haptics. These plate haptics usually made from silicone, are solid, flat, flexible and between 3.0 and 6.0 mm in width, 0.20 to 0.75 mm thick, and may have tapered, rounded or parallel sides. Plate haptics often have flexible loops or fingers that help center and fixate the lens within the capsular bag. These flexible fingers extend beyond the distal or outer end of the plate haptics and slightly beyond the diameter of the capsular bag and are designed to flex centrally to center and fixate the lens and its optic within the capsular bag.

An intraocular lens (IOL) is a lens implanted into the eye, usually replacing a normal human lens that has been clouded over by a cataract, or can replace a normal human lens as a form of refractive surgery to change the eye's optical power.

An accommodating IOL (AIOL) permits refocusing of the eye by means of movement along the optical axis in response to the constriction or relaxation of ciliary muscles. Near vision results from a forward movement of the optic upon constriction of the ciliary muscle which increases the pressure in the posterior part of the eye with a simultaneous decrease in pressure in the anterior part of the eye. Distance vision results from the reverse pressure change that takes place upon relaxation of the ciliary muscle and the resultant backwards movement of the lens. The movement of the optic enables the patient implanted with the lens to automatically change their vision between far, intermediate and near.

AIOLs are known to consist of opposing haptics positioned on either side of a lens optic. Once a patient's cataract is removed, by e.g. phacoemulsification, the IOL is placed into the empty capsular bag. The haptics help to center the IOL and fixate it within the capsular bag by fibrosis. Such AIOLs are described in U.S. Pat. No. 5,674,282, U.S. Pat. No. 5,476,514, and U.S. Pat. No. 5,496,366, to Cumming, herein incorporated by reference in its entirety.

And although current AIOLs provide patients with significantly restored distance and intermediate vision, adequate near vision is commonly lacking—often requiring that patients use weak reading glasses to enhance near vision. Multi-focal and toric lens solutions suffer from the disadvantages identified above.

SUMMARY OF THE INVENTION

An accommodating intraocular lens according to an embodiment of the present invention is described that overcomes the deficiencies of present designs noted above.

The field of the invention is a single focus accommodating intraocular lens that provides seamless vision from distance to near automatically by relaxation and constriction of the ciliary muscle.

An accommodating intraocular lens is provided whose lens optic is coupled to at least one haptic and is biased with respect thereto. The accommodating intraocular lens may have an optic coupled to a plate haptic via a member that substantially promotes the optic's response to a vitreous pressure change.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

Illustrated in the accompanying drawing(s) is at least one of the best mode embodiments of the present invention In such drawing(s):

FIGS. 3A and 3B illustrate side plan views of AIOL vaulting according to at least one embodiment of the present invention;

DETAILED DESCRIPTION OF THE PREFERRED EMBODIMENTS

The above described drawing figures illustrate the described invention in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present invention.

A preferred embodiment will now be described with reference to FIG. 1.

An accommodating intraocular lens (AIOL) 100 comprises: an optic 200 coupled to at least one haptic 300 such that the optic 200 is biased with respect to the haptic 300.

The AIOL 100 is placed into the capsular bag of a patient's eye after cataract surgery via known techniques such as, for example, phacoemulsification. The lens is centered so that the optical axis of the lens coincides with that of the patient's eye. The haptics 300 contact the capsular bag and the natural fibrosis of the tissue secures the haptics 300, and consequently the AIOL 100, in place.

The optic 200 is preferably a single focus optic that gathers the incoming light and focuses it on the retina of the patient so as to effect vision. The optic 200 may be bioconvex, refractive, diffractive, plano-convex, Fresnell, spheric, aspheric, toric, or of any other type that is substantially single focus. In order to permit the optic 200 to be inserted into the eye through a small incision, the optic 200 is preferably made of a flexible optical material, such as, for example, silicone, acrylic, hydrogel, or other flexible optical material now known or hereafter developed.

Figure 1:
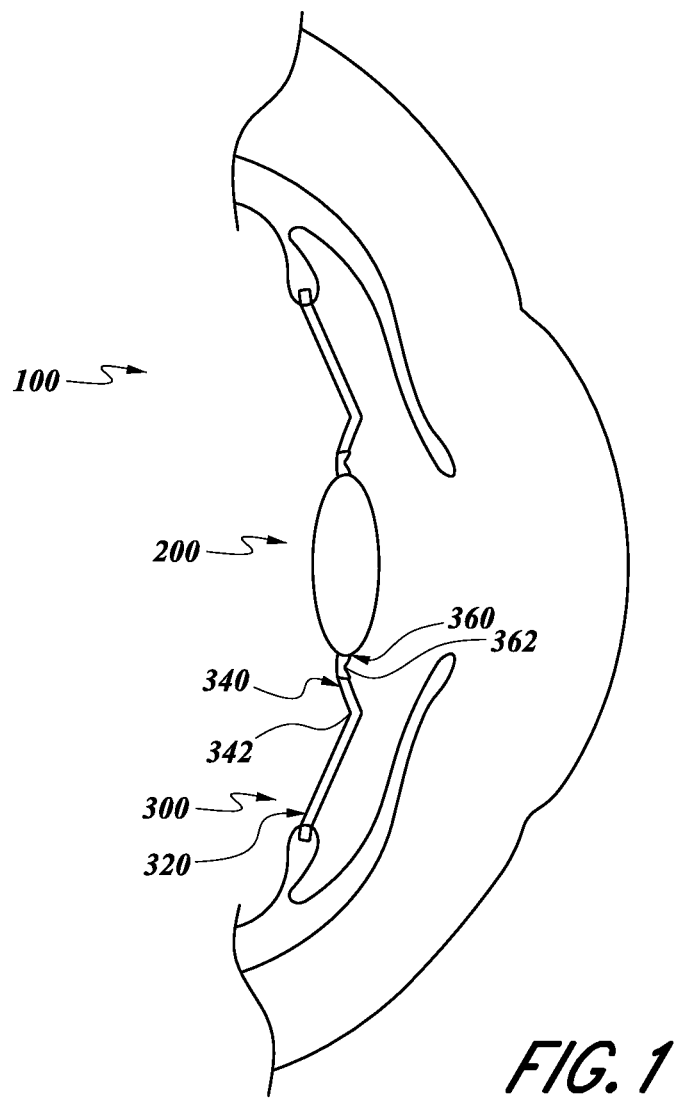
FIG. 1 illustrates a side plan view of an AIOL as inserted into a human eye, according to at least one embodiment of the present invention.

As shown in FIG. 1, the optic 200 is coupled to at least one haptic 300 having distal 320 and proximal 340 ends. A flexion 342 biases the optic 200 with respect to the distal end 320 of the haptic 300, and comprises the proximal end 340 set at a non-straight angle with respect to the distal end 320.

In a preferred embodiment, the flexion 342 biases the optic 200 anteriorly with respect to the distal end 320 and sets a positive angle between the proximal 340 and distal 320 ends, as measured from the direction of the optic 200. Thus, while the inserted AIOL 100 is in a neutral state (i.e. one with little to no vitreous pressure applied in either direction) the optic 200 is anteriorly biased—that is, the optic 200 is more anterior (or forward) than the proximal end 340 of the haptic 300.

In an alternative embodiment, the flexion 342 biases the optic 200 posteriorly with respect to the distal end 320 and sets a negative angle between the proximal 340 and distal 320 ends, as measured from the direction of the optic 200. Thus, while the inserted AIOL 100 is in a neutral state the optic 200 is posteriorly biased—that is, the optic 200 is more posterior (or rearward) than the proximal end 340 of the haptic 300.

In some embodiments, the optic 200 may be coupled in series with opposing haptics 300 and may be anteriorly biased with respect to one while posteriorly biased to the other. However, whether wholly posterior, wholly anterior, or partially posterior and partially anterior, the bias operates to increase the range of accommodation that would otherwise be present, as discussed herein. For example, with an anterior bias the optic 200 requires less vitreous pressure and ciliary muscle contraction to move to the same forward position as without the bias. Thus, patients whose eyes are not able to exert the necessary pressure for optimal near vision with non-biased AIOLs can nonetheless exert the pressure required for optimal near vision with anteriorly biased AIOLs 100.

Turning again to FIG. 1, the haptic 300 may be coupled to the optic via a connecting portion 360 made of the same flexible material of the optic 200. The connecting portion 360 may comprise a hinge 362 that traverses the connecting portion 360 that operates to weaken the connecting portion 360 so that vitreous pressure and end-to-end compression of opposing haptics 300 can stretch the base of the hinge 362 like an elastic band to allow the optic 200 to move forward. This increases the range of focusing abilities—especially in the near range. Because the lens can move further forward, near focus is improved. The connecting portion 360 may also comprise one or more straps. The straps further assist in accommodation in that they decrease the resistance to the pressure that pushes the optic forward. Exemplary connecting portions are described in U.S. patent Ser. Nos. 13/017,189; 13/092,359; 13/111,599; and 13/155,327, incorporated herein by reference in their entireties.

In at least one embodiment, the connecting portion 360, for example, the flexible extension of the optic 200 coupling the optic to the haptic 300, may have a flexible hinge 362 extending transversely across either or both sides.

Figure 2A:
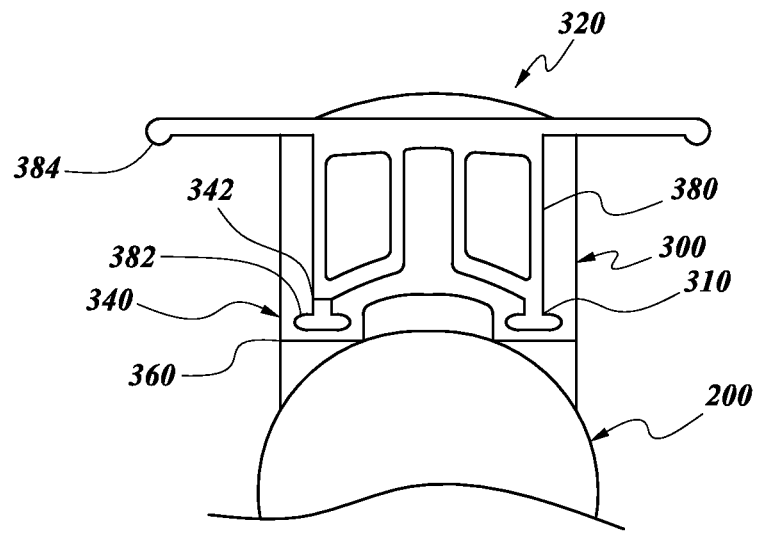
FIGS. 2A and 2B illustrate top plan views of various AIOLs according to at least one embodiment of the present invention.
Figure 2B:
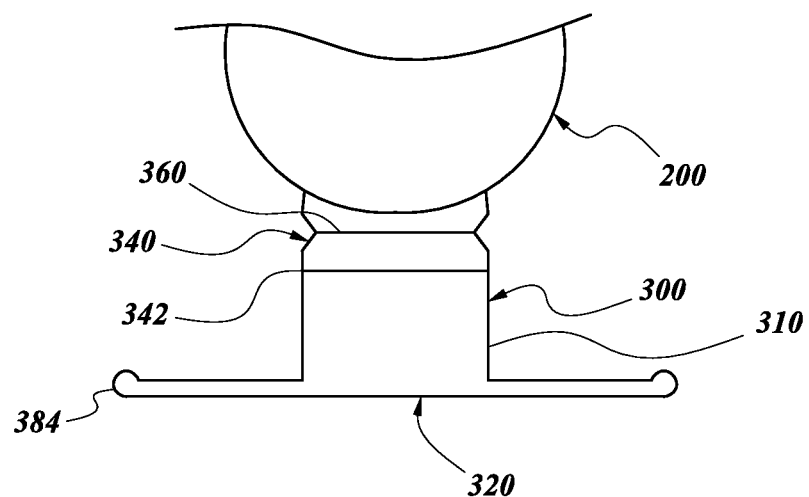

Turning now to FIGS. 2A and 2B, the at least one haptic 300 is preferably a plate haptic comprising: a body 310, having distal 320 and proximal 340 ends angularly set so as to form the substantially rigid flexion 342.

The plate haptic 300 may comprise projections 384, the haptic and projections operable to engage, fixate and center the haptic into the capsular bag. Since, on insertion into the eye, the AIOL is vaulted posteriorly, the plate haptic moves centrally and posteriorly in response to ciliary muscle contraction, as shown in FIGS. 3A and 3B, such movement, combined with the change in vitreous pressure, causing the optic to vault anteriorly. The haptic body may be substantially flexible in the transverse direction and substantially rigid in the longitudinal direction so as to enable the AIOL 100 to be folded and inserted into the eye via a small incision. One of ordinary skill will appreciate that while substantial rigidity may promote vaulting; the degree of rigidity imposed is not intended to preclude an effective vault of the optic at the connecting portion 360. It is preferable that the haptic body be constructed of the same or similar flexible material as the optic, including, but not limited to: silicone, hydrogel, acrylic, or similar material. Non-biased plate haptics having similar features are discussed in U.S. patent Ser. Nos. 13/017, 189; 13/092,359; 13/111,599; and 13/155,327, incorporated herein by reference in their entireties.

Returning now to FIGS. 2A and 2B, a frame 380 may be embedded within the haptic body so as to promote the longitudinal rigidity thereof. The frame 380 may be formed of polyimide, prolene, polymethylmethanylate (PMMA), titanium, or similar material. Such exemplary frames are discussed in U.S. patent Ser. Nos. 13/017,189; 13/092,359; 13/111,599; and 13/155,327, incorporated herein by reference in their entireties. As shown in FIGS. 2A and 2B, the frame 380 may comprise an anchor 382 extending into the proximal end 340 of the haptic 300 and forming the flexion with the distal end 320 and associated rest of the frame 380. The anchor 382 operates to set and maintain the angle of the flexion 342.

As shown in FIGS. 2A and 2B, the haptic 300 may comprise projections 384, or fingers, extending from the distal end 320 to engage the capsular bag and secure and center the AIOL 100 thereto. The projections 384 may be homogeneous with the frame 380 and may be made of either polyimide, PMMA, acrylic or any other inert material. In some embodiments, the projections may be molded into the flexible plate haptic 300 as a T-shaped cross bar projection. Such exemplary projections are discussed in U.S. patent Ser. Nos. 13/017,189; 13/092,359; 13/111,599; and 13/155,327, incorporated herein by reference in their entireties.

As discussed herein, the haptic 300 may be coupled to the optic via connecting portion 360 that operates to permit contraction of the ciliary muscles to cause an end-to-end compression of opposing haptics with an increase in vitreous pressure, thus moving the optic substantially forward.

In at least one embodiment, the longitudinal length of the IOL (i.e. from distal end to distal end) may be between approximately 9.0-11.0 mm, with the diameter as measured from the tips of the lateral projections being between approximately 11.5-12.0 mm. The haptics 300 are preferably between 3.0-6.0 mm wide and 0.20-0.75 mm thick, while the optic may be approximately 5.0 mm.

In a preferred embodiment, the plate haptic 300 are designed to be flexible transversely, but rigid longitudinally. At the distal ends 320 of the plate haptics 300 are transverse flexible arms 384 designed to center and fixate the AIOL 100 within the capsular bag. The rigid polyimide frame 380 molded within the plate haptic may be flexed anteriorly at the proximal end and is designed to push the edge of the optic 200 forwards upon end-to-end compression of the AIOL 100 with contraction of the ciliary muscle.

In at least one embodiment, the rigid plate haptics 300 are flat, with the rigid flexion 382 in the longitudinal rigid frame 380 molded into the transversely flexible plate haptic 300, the flexion 382 being located at the proximal end 320 of the haptic body 310 across the width of the rigid components 380 in the haptic body 310, as seen, for example, in FIG. 1.

In at least one embodiment, the plate haptic 300 is curved, with a rigid curve in the longitudinal rigid frame 380 molded into the transversely flexible plate haptic 300, as seen, for example in FIGS. 3A and 3B. In at least one embodiment the longitudinally rigid plates 300 are bowed backwards when the AIOL 100 is placed into the eye.

In at least one embodiment, the optic 200 will move forward upon constriction of the circular ciliary muscle which increases vitreous pressure and with the reduction in its diameter applies end-to-end pressure on the haptics 300. Relaxation of the ciliary muscle causes an increase in the diameter of the ciliary muscle and a reduction in vitreous cavity pressure with an increase in pressure in the anterior part of the eye such that the optic 200 moves posteriorly to the distant vision position.

Turning now to FIG. 5, the AIOL 100 is shown where the optic 200 is coupled in series to opposing plate haptics 300— one rigid and one flexible, the rigid plate haptic being positioned at the 12 o'clock position in the eye and the flexible plate haptic being positioned at the 6 o'clock position in the eye. As discussed herein, the rigid plate haptic 300 preferably comprises a frame 380 that in turn preferably comprises the flexion 382 located at the proximal end 320 biasing the optic 200 such that the center of the optic 200 is anterior, or in front of the plate haptic 300 having such a flexion 382. The proximal end 320 of the rigid plate haptic 300 may be molded into the connecting portion 360—which may be a flexible extension of the optic 200—during the manufacturing molding process. Further, as discussed herein, each plate haptic 300 may have one or more flexible projections or fingers 384 extending from the distal ends 320 thereof. Still further, as discussed herein, respective hinges 362 of the connecting portions 360 of both haptics 300 are preferably provided so as to permit improved response to vitreous pressure changes. As discussed herein, one or more straps may couple the plate haptic 300 to the optic 200. The straps may comprise grooves or hinges that traverse the strap and promote accommodation.

The enablements described in detail above are considered novel over the prior art of record and are considered critical to the operation of at least one aspect of the invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that the named inventor believes that the claimed subject matter is what is intended to be patented.

What is claimed is:

1. An accommodating intraocular lens (IOL) adapted to be placed into the capsular bag of a patient's eye after cataract surgery, said intraocular lens comprising:
  a first plate haptic and an opposite second plate haptic, each of said opposing first and second haptics comprising a haptic body having a distal end and a proximal end, the first plate haptic adapted to be positioned at a twelve o'clock position within the eye, and the second plate haptic adapted to be positioned at a six o'clock position within the eye;
  a single focus lens optic made of a flexible, stretchable optical material, the lens optic coupled to said opposing plate haptics;
  one or more flexible connecting portions coupling each haptic to the optic, the connecting portions having one or more hinges thereon traversing the one or more connecting portions;
  a single, monolithic reinforcement frame internal to one or both haptic bodies, the frame having a shape comprising of a plurality of longitudinal structures and at least one transverse structure,
    wherein the longitudinal structures are embedded within the haptic body and extend substantially the entire length of the haptic body;

wherein the at least one transverse structure is at least partially embedded within the haptic body and extends laterally and exposed from the distal end of each plate haptic as centration fingers;

wherein the shape of the frame causes the haptic body to be more rigid in a longitudinal direction than in a transverse direction, and more flexible in the transverse direction than in the longitudinal direction; and wherein each haptic comprises a substantially rigid flexion that sets the proximal and distal ends of the haptic body in a non-zero angle with respect to each other so as to bias the optic with respect to the haptics.

2. The accommodating intraocular lens of claim 1, wherein the bias is an anterior bias.

3. The accommodating intraocular lens of claim 1, wherein the bias is a posterior bias.

4. The accommodating intraocular lens of claim 1, wherein the haptics are flat.

\* \* \* \* \*